United States Patent
Tropello (10) Patent No.: US 12,161,363 B2
(45) Date of Patent: Dec. 10, 2024

(54) METHOD AND APPARATUS FOR COAPTIVE ULTRASOUND GASTROSTOMY

(71) Applicant: University of Maryland, Baltimore, Baltimore, MD (US)

(72) Inventor: Steven Tropello, Baltimore, MD (US)

(73) Assignee: University of Maryland, Baltimore, Baltimore, MD (US)

( * ) Notice: Subject to any disclaimer, the term of this patent is extended or adjusted under 35 U.S.C. 154(b) by 0 days.

(21) Appl. No.: 17/682,449

(22) Filed: Feb. 28, 2022

(65) Prior Publication Data

US 2023/0047272 A1 Feb. 16, 2023

Related U.S. Application Data

(63) Continuation of application No. 16/152,059, filed on Oct. 4, 2018, now Pat. No. 11,259,838, which is a
(Continued)

(51) Int. Cl.
*A61B 17/34* (2006.01)
*A61J 15/00* (2006.01)
*A61M 25/10* (2013.01)

(52) U.S. Cl.
CPC ....... *A61B 17/3415* (2013.01); *A61J 15/0015* (2013.01); *A61M 25/1018* (2013.01);
(Continued)

(58) Field of Classification Search
CPC .............. A61B 8/0841; A61B 17/3415; A61B 2017/3486; A61B 2017/3413;
(Continued)

(56) References Cited

U.S. PATENT DOCUMENTS

| 3,961,632 A | 6/1976 | Moossun |
| 4,077,412 A | 3/1978 | Moossun |

(Continued)

FOREIGN PATENT DOCUMENTS

| CN | 105939693 A | 9/2016 |
| EP | 0371486 A1 | 6/1990 |

(Continued)

OTHER PUBLICATIONS

Arias, Elizabeth, et al. "United States Life Tables, 2005." National Vital Stat Reports. vol. 58, No. 10., Mar. 2010, 132 pages.
(Continued)

*Primary Examiner* — Theodore J Stigell (57) ABSTRACT

Disclosed is a system and method for the placement of elongate medical members within a patients body using coaptive ultrasound. In a particularly preferred embodiment, a flexible tube includes a first balloon at a distal end of the tube, and a second balloon at the distal end of the tube and positioned within the first balloon. The first and second balloons are inflatable to form one or more echogenic windows between them, which echogenic window may be detected from within a patient's body by an ultrasound probe that is external to the patient's body. Detection of such echogenic window is used to identify an acceptable location on the patient's body at which to insert a guidewire configured to receive an elongate medical member without damage to surrounding patient tissues or organs.

17 Claims, 5 Drawing Sheets

Related U.S. Application Data continuation of application No. PCT/US2017/026141, filed on Apr. 5, 2017.

(60) Provisional application No. 62/318,449, filed on Apr. 5, 2016.

(52) U.S. Cl.
CPC ... *A61M 25/104* (2013.01); *A61B 2017/3413* (2013.01); *A61B 2017/3486* (2013.01)

(58) Field of Classification Search
CPC ............ A61J 15/0015; A61J 15/00158; A61M 25/1018; A61M 25/104; A61M 2025/1013
See application file for complete search history.

(56) References Cited

U.S. PATENT DOCUMENTS

| | | | |
|---|---|---|---|
| 4,403,612 A | 9/1983 | Fogarty | |
| 5,058,580 A | 10/1991 | Hazard | |
| 5,112,310 A | 5/1992 | Grobe | |
| 5,154,387 A | 10/1992 | Trailer | |
| 5,265,622 A | 11/1993 | Barbere | |
| 5,269,291 A | 12/1993 | Carter | |
| 5,431,640 A | 7/1995 | Gabriel | |
| 5,458,583 A | 10/1995 | McNeely et al. | |
| 5,497,782 A | 3/1996 | Fugoso | |
| 5,564,360 A | 10/1996 | Wright | |
| 5,653,230 A | 8/1997 | Ciaglia et al. | |
| 5,669,380 A | 9/1997 | Garry et al. | |
| 5,681,260 A | 10/1997 | Ueda et al. | |
| 5,915,383 A | 6/1999 | Pagan | |
| 6,015,414 A | 1/2000 | Werp et al. | |
| 6,058,323 A | 5/2000 | Lemelson | |
| 6,126,647 A | 10/2000 | Posey et al. | |
| 6,173,199 B1 | 1/2001 | Gabriel | |
| 6,428,551 B1 | 8/2002 | Hall et al. | |
| 6,651,665 B1 | 11/2003 | Sellers et al. | |
| 6,685,671 B1 | 2/2004 | Oishi et al. | |
| 6,701,918 B2 | 3/2004 | Fariss et al. | |
| 6,702,804 B1 | 3/2004 | Ritter et al. | |
| 6,746,465 B2 * | 6/2004 | Diederich ............ A61M 29/02 604/101.02 |
| 6,916,284 B2 | 7/2005 | Moriyama | |
| 7,066,924 B1 | 6/2006 | Garibaldi et al. | |
| 7,757,694 B2 | 7/2010 | Ritter et al. | |
| 7,761,133 B2 | 7/2010 | Viswanathan et al. | |
| 7,769,428 B2 | 8/2010 | Viswanathan et al. | |
| 7,853,306 B2 | 12/2010 | Viswanathan et al. | |
| 7,963,910 B2 | 6/2011 | Okada | |
| 8,075,519 B2 | 12/2011 | Min et al. | |
| 8,088,129 B2 | 1/2012 | Werp et al. | |
| 8,226,637 B2 | 7/2012 | Satake | |
| 8,419,681 B2 | 4/2013 | Sell | |
| 8,677,990 B2 | 3/2014 | Gabriel | |
| 8,764,769 B1 | 7/2014 | Rodriguez-Navarro et al. | |
| 8,790,245 B2 | 7/2014 | Rodriguez et al. | |
| 8,834,370 B2 | 9/2014 | Evert et al. | |
| 8,997,748 B2 | 4/2015 | Margolin et al. | |
| 10,219,778 B2 | 3/2019 | Tropello | |
| 10,383,595 B2 | 8/2019 | Tropello | |
| 11,259,838 B2 | 3/2022 | Tropello | |
| 11,612,546 B2 | 3/2023 | Tropello et al. | |
| 2002/0055757 A1 | 5/2002 | Torre et al. | |
| 2003/0040671 A1 | 2/2003 | Somogyi et al. | |
| 2003/0066532 A1 | 4/2003 | Gobel | |
| 2004/0255954 A1 | 12/2004 | Zgoda et al. | |
| 2005/0209682 A1 | 9/2005 | Abraham-Fuchs et al. | |
| 2006/0009735 A1 | 1/2006 | Viswanathan et al. | |
| 2006/0025675 A1 | 2/2006 | Viswanathan et al. | |
| 2006/0025676 A1 | 2/2006 | Viswanathan et al. | |
| 2006/0025719 A1 | 2/2006 | Viswanathan et al. | |
| 2006/0247530 A1 | 11/2006 | Hardin, Jr. et al. | |
| 2007/0021685 A1 | 1/2007 | Oepen et al. | |
| 2007/0135825 A1 | 6/2007 | Binmoeller | |
| 2007/0205785 A1 | 9/2007 | Nilsson | |
| 2008/0045863 A1 | 2/2008 | Bakos | |
| 2008/0194994 A1 | 8/2008 | Bown et al. | |
| 2008/0294102 A1 | 11/2008 | Cartledge et al. | |
| 2009/0012517 A1 | 1/2009 | De et al. | |
| 2009/0062772 A1 | 3/2009 | Wakeford et al. | |
| 2009/0099583 A1 | 4/2009 | Butterfield et al. | |
| 2009/0157066 A1 | 6/2009 | Satake | |
| 2009/0187164 A1 | 7/2009 | Rowe | |
| 2009/0198153 A1 | 8/2009 | Shriver | |
| 2010/0094116 A1 | 4/2010 | Silverstein | |
| 2010/0145147 A1 | 6/2010 | Pinsky et al. | |
| 2010/0179510 A1 | 7/2010 | Fox et al. | |
| 2010/0234668 A1 * | 9/2010 | Roeder ................ A61N 5/1015 600/3 |
| 2010/0318094 A1 * | 12/2010 | Oishi .................. A61B 17/3415 606/108 |
| 2012/0143029 A1 | 6/2012 | Silverstein et al. | |
| 2012/0197062 A1 | 8/2012 | Requarth | |
| 2012/0203175 A1 | 8/2012 | Sun | |
| 2012/0253102 A1 | 10/2012 | Marban et al. | |
| 2012/0265130 A1 | 10/2012 | De et al. | |
| 2013/0047993 A1 | 2/2013 | Lally | |
| 2013/0053770 A1 | 2/2013 | Aggerholm et al. | |
| 2013/0060127 A1 | 3/2013 | Burton et al. | |
| 2013/0072792 A1 | 3/2013 | Aggerholm et al. | |
| 2013/0109957 A1 | 5/2013 | 'T Hooft et al. | |
| 2013/0184571 A1 | 7/2013 | Wilkening et al. | |
| 2014/0039358 A1 | 2/2014 | Zhou et al. | |
| 2014/0180242 A1 | 6/2014 | Tai | |
| 2014/0180252 A1 | 6/2014 | Gabriel | |
| 2014/0200504 A1 * | 7/2014 | Rocha-Singh ......... A61N 5/062 604/509 |
| 2014/0228680 A1 | 8/2014 | Fukuda | |
| 2014/0276941 A1 | 9/2014 | Rodriguez-Navarro et al. | |
| 2015/0045615 A1 | 2/2015 | Bates et al. | |
| 2015/0238729 A1 | 8/2015 | Jenson et al. | |
| 2016/0038008 A1 | 2/2016 | Molnar | |
| 2016/0081652 A1 | 3/2016 | Tropello | |
| 2016/0213870 A1 | 7/2016 | Kumar et al. | |
| 2016/0279393 A1 | 9/2016 | Anderson et al. | |
| 2016/0302811 A1 | 10/2016 | Rodriguez-Navarro et al. | |
| 2017/0050040 A1 | 2/2017 | Trembly | |
| 2018/0078234 A1 | 3/2018 | Tropello | |
| 2018/0272090 A1 | 9/2018 | Blom | |
| 2019/0167298 A1 | 6/2019 | Tropello | |
| 2019/0239727 A1 | 8/2019 | Tozzi et al. | |
| 2020/0214661 A1 | 7/2020 | Tropello | |
| 2021/0052855 A1 | 2/2021 | Kiselyov et al. | |
| 2021/0244482 A1 | 8/2021 | Tropello et al. | |
| 2021/0244624 A1 | 8/2021 | Tropello et al. | |
| 2021/0275766 A1 | 9/2021 | Tropello et al. | |
| 2021/0393911 A1 | 12/2021 | Cohen et al. | |
| 2023/0181151 A1 | 6/2023 | Tropello | |
| 2023/0191061 A1 | 6/2023 | Tropello et al. | |
| 2023/0404857 A1 | 12/2023 | Tropello et al. | |

FOREIGN PATENT DOCUMENTS

| | | |
|---|---|---|
| EP | 2604191 A1 | 6/2013 |
| IT | MI20111820 A1 | 4/2013 |
| JP | H06503243 A | 4/1994 |
| JP | H0889582 A | 4/1996 |
| JP | H0889583 A | 4/1996 |
| JP | H08117232 A | 5/1996 |
| JP | H10118181 A | 5/1998 |
| JP | H1156852 A | 3/1999 |
| JP | 2000512873 A | 10/2000 |
| JP | 2003093332 A | 4/2003 |
| JP | 2004283606 A | 10/2004 |
| JP | 3806601 B2 | 8/2006 |
| JP | 2008284136 A | 11/2008 |
| JP | 2009232917 A | 10/2009 |
| JP | 2010532669 A | 10/2010 |
| JP | 2012501689 A | 1/2012 |
| JP | 2012502749 A | 2/2012 |
| JP | 2013121390 A | 6/2013 |
| JP | 2015061550 A | 4/2015 |

(56) References Cited

FOREIGN PATENT DOCUMENTS

| | | |
|---|---|---|
| JP | 2016522021 A | 7/2016 |
| JP | 2017023199 A | 2/2017 |
| WO | WO-9748438 A2 | 12/1997 |
| WO | WO-9936120 A1 | 7/1999 |
| WO | WO-2006005012 A2 | 1/2006 |
| WO | WO-2010033629 A1 | 3/2010 |
| WO | WO-2010036721 A2 | 4/2010 |
| WO | WO-2010129327 A1 | 11/2010 |
| WO | WO-2012003665 A1 | 1/2012 |
| WO | WO-2014176236 A1 | 10/2014 |
| WO | WO-2017176881 A1 | 10/2017 |
| WO | WO-2017216650 A1 | 12/2017 |
| WO | WO-2018002933 A1 | 1/2018 |
| WO | WO-2018082980 A1 | 5/2018 |
| WO | WO-2019210170 A1 | 10/2019 |
| WO | WO-2019213657 A1 | 11/2019 |
| WO | WO-2019232398 A1 | 12/2019 |
| WO | WO-2020005186 A2 | 1/2020 |
| WO | WO-2021051051 A1 | 3/2021 |
| WO | WO-2021258052 A1 | 12/2021 |
| WO | WO-2023023360 | 2/2023 |
| WO | WO-2023102226 A1 | 6/2023 |
| WO | WO-2023133552 A2 | 7/2023 |

OTHER PUBLICATIONS

Arora, Gaurav, et al. Percutaneous Endoscopic Gastrostomy (PEG) Tube Placement. Dec. 27, 2012. Updated Dec. 14, 2015. http://emedicine.medscape.com/article/149665-overview, 2 pages.
Duszak, Richard, et al. "Percutaneous Gastrostomy and Jejunostomy." Dec. 27, 2012. Updated Jan. 14, 2014. http://emedicine.medscape.com/article/1821257-overview, 4 pages.
Extended European Search Report issued by the European Patent Office for Application No. 14788472, dated Dec. 21, 2016, 7 pages.
Extended European Search Report issued by the European Patent Office for Application No. 18177361.5, dated Jan. 23, 2019, 8 pages.
Extended European Search Report issued by the European Patent Office for Application No. 19793773.3, dated Feb. 2, 2022, 7 pages.
Extended European Search Report issued by the European Patent Office for Application No. 19797039.5, dated Jan. 4, 2022, 7 pages.
Extended European Search Report issued by the European Patent Office for Application No. 19811977.8, dated Feb. 9, 2022, 7 pages.
Gauderer, Michael W. L. "Percutaneous endoscopic gastrostomy—20 years later: a historical perspective." Journal of Pediatric Surgery, Jan. 2001; 36: 217-219.
International Search Report and Written Opinion for International Application No. PCT/US2021/038263, mailed Oct. 14, 2021, 10 pages.
International Search Report and Written Opinion issued by the International Examining Authority for Application No. PCT/US2014/034950, dated Oct. 1, 2014, 8 pages.
International Search Report and Written Opinion issued by the International Examining Authority for Application No. PCT/US2017/026141, dated Aug. 25, 2017, 11 pages.
International Search Report and Written Opinion issued by the International Examining Authority for Application No. PCT/US2019/029351, dated Jul. 17, 2019, 9 pages.
International Search Report and Written Opinion issued by the International Examining Authority for Application No. PCT/US2019/030902, dated Jul. 18, 2019, 7 pages.
International Search Report and Written Opinion issued by the International Examining Authority for Application No. PCT/US2019/034943, dated Aug. 27, 2019, 7 pages.
Japanese Patent Application No. 2019-238125, Office Action mailed Sep. 14, 2021, 6 pages—English Translation Available.
Lohsiriwat, Varul. "Percutaneous endoscopic gastrostomy tube replacement: A simple procedure?" World Journal of Gastrointestinal Endoscopy, Jan. 16, 2013; 5: 14-18.
Lynch, C.R. and J.C. Fang. "Prevention and Management of Complications of PEG tubes." Practical 3astroenterology, Nov. 2004; 66-76.
Notice of Allowance issued by the United States Patent and Trademark Office for U.S. Appl. No. 14/785,366 dated May 13, 2019, 8 pages.
Notice of Allowance issued by the United States Patent and Trademark Office for U.S. Appl. No. 15/809,665 dated Nov. 29, 2018, 7 pages.
Office Action for Chinese application No. CN20198040162, mailed on Jul. 29, 2022, 19 pages.
Office Action issued by the Japanese Patent Office for Application No. 2016-510734, dated Dec. 11, 2018, 10 pages (including 5 page English translation).
Office Action issued by the Japanese Patent Office for Application No. 2016-510734, dated Jan. 30, 2018, 12 pages (including 6 page English translation).
Office Action issued by the Japanese Patent Office for Application No. 2019-238125, dated Jan. 12, 2021, 4 pages.
Office Action issued by the United States Patent and Trademark Office for U.S. Appl. No. 14/785,366, dated Jan. 11, 2019, 11 pages.
Office Action issued by the United States Patent and Trademark Office for U.S. Appl. No. 14/785,366, dated Jun. 13, 2018, 12 pages.
Office Action issued by the United States Patent and Trademark Office for U.S. Appl. No. 15/809,665 dated Jun. 14, 2018, 8 pages.
Park et al., "Simple and Safe Foley Catheter-Guided Tracheostomy Tube Changes", ResearchGate Trauma Image Proced, Nov. 2018(2), pp. 72-75, https://www.researchgate.net/publication/331070429 Simple_and_Safe_Foley_Catheter-Guided_Tracheostomy_Tube_Changes.
Rosenberger, Laura H., et al. "Late accidental dislodgement of a percutaneous endoscopic gastrostomy tube: an underestimated burden on patients and the health care system." Surgical Endoscopy, Oct. 2011; 25: 3307-3311.
Tsukuda, Toshinobu, et al. "Percutaneous Radiologic Gastrostomy Using Push-Type Gastrostomy Tubes with CT and Fluoroscopic Guidance." Interventional Radiology, Feb. 2006; 186: 574-576.
Gray, et al., "Direct percutaneous jejunostomy", AJR Am J Roentgenol., Nov. 1987;149(5): 931-2.
International Search Report and Written Opinion for International Application No. PCT/US2022/040941 mailed Dec. 15, 2022, 16 pages.
International Search Report and Written Opinion for International Application No. PCT/US2022/051714 dated Mar. 21, 2023, 16 pages.
International Search Report and Written Opinion for International Application No. PCT/US2023/060313, mailed on Jun. 23, 2023, 15 pages.
Invitation to Pay Fee for International Application No. PCT/US2023/060313 dated Apr. 19, 2023, 2 pages.
Kim, et al. "Comparison of primary jejunostomy tubes versus gastrojejunostomy tubes for percutaneous enteral nutrition", J Vasc Interv Radiol. Dec. 24, 2013 (12): 1845-52.
Non-Final Office Action for U.S. Appl. No. 17/087,150 dated Apr. 26, 2023, 14 pages.
Non-Final Office Action for U.S. Appl. No. 17/945,971 dated Mar. 30, 2023, 7 pages.
Notice of Allowance issued in U.S. Appl. No. 16/152,059, mailed Oct. 27, 2021, 4 pgs.
Notice of Allowance issued in U.S. Appl. No. 17/080,441, mailed Nov. 9, 2022, 10 pgs.
Office Action—Restriction Requirement—issued by The United States Patent and Trademark Office for U.S. Appl. No. 15/809,665, dated Feb. 12, 2018, 6 pages.
Office Action for Japanese Application No. JP20200566906 dated Apr. 26, 2023, 6 pages.
Office Action for Japanese Application No. JP20210509720 mailed on Mar. 27, 2023, 10 pages.
Office Action for Japanese Application No. JP20210512365 dated Mar. 13, 2023, 7 pages.
Office Action for Japanese Application No. JP20220091041 dated Jun. 6, 2023, 5 pages.
Office Action issued in U.S. Appl. No. 16/544,518, mailed Mar. 17, 2022, 5 pgs.

(56) References Cited

OTHER PUBLICATIONS

Office Action issued in U.S. Appl. No. 17/080,441, mailed May 9, 2022, 18 pgs.

Panagiotakis, et al., "DPEJ tube placement prevents aspiration pneumonia in high-risk patients", Nutr Clin Pract Apr.-May 2008; 23 (2): 172-5.

Van Overhagen, et al. "US and fluoroscopic-guided percutaneous jejunostomy: experience in 49 patients", J Vasc Interv Radiol., Jan. 2000 11(1): 101-6.

Office Action issued by the Japanese Patent Office for Application No. 2019-238125, dated Jan. 12, 2021, 8 pages.

Office Action issued by the Japanese Patent Office for Application No. 2019-238125, dated Sep. 14, 2021, 8 pages.

Extended European Search Report for European Application No. EP20230184845 dated Jan. 30, 2024, 7 pages.

International Preliminary Report on Patentability for International Application No. PCT/US2022/040941 dated Feb. 29, 2024, 15 pages.

Non-Final Office Action for U.S. Appl. No. 17/087,150 dated Jan. 29, 2024, 19 pages.

Notice of Allowance for U.S. Appl. No. 17/945,971 dated Jan. 8, 2024, 9 pages.

Office Action and Search report for Chinese Application No. CN201980044942.0 dated Dec. 28, 2023, 21 pages.

Office Action for Australian Application No. AU20190257771 mailed Dec. 18, 2023, 4 pages.

Office Action for Australian Application No. AU20190262681 mailed Dec. 15, 2023, 5 pages.

Office Action for Australian Application No. AU20190277685 mailed Mar. 1, 2024, 4 pages.

Office Action for Japanese Application No. JP20210509720 mailed Oct. 18, 2023, 6 pages.

Office Action for Japanese Application No. JP20210512365 mailed Dec. 22, 2023, 11 pages.

Office Action for Japanese Application No. JP20220091041 dated Jan. 9, 2024, 5 pages.

Restriction Requirement for U.S. Appl. No. 17/108,200, mailed Oct. 13, 2023, 10 pages.

Non-Final Office Action for U.S. Appl. No. 17/108,200 dated Apr. 29, 2024, 18 pages.

\* cited by examiner

METHOD AND APPARATUS FOR COAPTIVE ULTRASOUND GASTROSTOMY

CROSS-REFERENCE TO RELATED APPLICATIONS

This application is a continuation of U.S. patent application Ser. No. 16/152,059, entitled "Method and Apparatus for Coaptive Ultrasound Gastrostomy," filed on Oct. 4, 2018 (now U.S. Pat. No. 11,259,838), which is a continuation of International PCT Application No. PCT/US2017/026141, entitled "Method and Apparatus for Coaptive Ultrasound Gastrostomy," filed on Apr. 5, 2017, which is based upon and claims priority from U.S. Provisional Patent Application Ser. No. 62/318,449 entitled "Method and Apparatus for Coaptive Ultrasound Gastrostomy," filed with the United States Patent and Trademark Office on Apr. 5, 2016, by the inventor herein, the specification of each of which is incorporated herein by reference in its entirety.

FIELD OF THE INVENTION

The present invention relates generally to placement of medical devices within a body in the medical field, and more particularly to methods and devices for ultrasound-guided placement of medical devices, such as catheters, conduits, carriers, electrodes, and the like, including a percutaneous gastrostomy tube, into a patient's body. Certain aspects of the invention particularly relate to methods and devices for ultrasound guided gastrostomy tube placement.

BACKGROUND OF THE PRIOR ART

A wide variety of medical procedures require placement of medical devices at various locations within a patient's body. For instance, certain procedures may require the placement of electrodes within a patient's spine, or attachment of electrodes to heart tissue, or the like. In other procedures, medical staff may wish to place temperature probes or heating wires at various locations within patient's body. Further, for cancer treatment, medical staff may wish to place radioactive seeds or deliver therapeutic medications deep within a patient's body, including directly into internal organs. In still other procedures, medical staff may wish to place catheters or other fluid or material-carrying conduits within the patient's body for delivery of medications or other materials, for carrying forceps, biopsy instruments or the like into the patient's body, for providing suctioning to various parts of a patient's body, and many other procedures involving the placement of medical devices within the patient's body. Procedures for placing such medical devices vary widely from application to application, but all carry the common aspect of presenting challenge to the medical staff in manipulating such medical devices within the patient's body to route them to their intended location and position them for their intended use at that location.

More particularly, often times medical procedures require manipulation of a catheter or other conduit through portions of the patient's body that are not easily accessible, and thus make maneuvering of the conduit to its intended location quite challenging. For instance, it may be medically necessary to place conduits within internal body cavities to provide for the drainage of unwanted fluid, to provide for the infusion of medications into internal organs or elsewhere in the body, to provide for direct nutritional supplementation to patients unable to orally consume adequate nutrition, and the like. The procedures for guiding such conduits to their intended locations in a patient's body can be difficult to perform and can risk serious injury to the patient if not performed properly.

One such procedure that presents significant challenges is the placement of gastrostomy tubes for patients requiring direct nutritional supplementation into the stomach. Enteral feeding has been recommended when a patient has a functioning gut but is unable to eat for seven to fourteen days. When enteral feeding is anticipated to be required for longer than 30 days, a gastrostomy tube is preferred over a nasoenteric tube. The placement of gastronomy tubes has become a frequently required procedure, with more than 215,000 being placed annually in the United States. The vast majority of such procedures are performed by consultants, such as gastroenterologists and interventional radiologists, as opposed to an emergency room doctor, an intensivist, or patient's primary physician. This is because those specialized consultant physicians have access to and have been trained on the expensive equipment that one must use to safely enter (i.e., cannulate) the stomach (i.e., gastrostomy). This expensive equipment includes endoscopes, fluoroscopes, and computed tomography (CT) scanners, all of which require specialized training and skill to operate properly.

The most common method for initial gastrostomy tube insertion is Percutaneous Endoscopic Gastrostomy ("PEG"), involving placing of a tube into the patient's stomach. When performing a typical PEG process, a patient is placed in the supine position. A nasal or oral gastric tube is then introduced into the patient's stomach. Gastric fluid is removed using suction, such as through fenestrations at the distal end of the nasal or oral gastric tube. The stomach is then insufflated by way of the gastric tube or an endoscope. In one method, the endoscope has a light at the distal end. When illuminated, the practitioner is supposed to identify a suitable puncture site that is free from interposed organs and large vessels by noting where the light from the endoscope shines through the abdominal skin of the patient. An incision is then made at the identified target site, and a sheathed needle is then entered into the insufflated stomach. A guide wire is then introduced through the abdominal sheath and into the stomach. A snare or forceps located at the distal end of the endoscope is manipulated to capture the end of the guide wire. The endoscope is then extracted, pulling the guide wire along and ultimately causing the guide wire to exit through the mouth or nose. Applicant is aware of two preferred methods to complete the gastrostomy after the guide wire has been routed from the outside of the patient's abdomen, into their stomach, up their esophagus and out through their mouth or nose: the Ponsky-Gauderer (pull-(on) string) method (the "PG method"), and the Sacks-Vine (push-over-wire) method (the "SV method").

If the PG method is selected, the gastrostomy tube is tied to the end of the guide wire that has exited through the patient's nose or mouth. The abdominal end of the guide wire is then pulled until the gastrostomy tube extends out from the hole in the abdomen, with the proximal end of the gastrostomy tube (having an enlarged end, or bumper, therein to prevent it from passing through the stomach wall and out of the patient's abdomen) remaining within and providing access to the interior of the patient's stomach. If the SV method is selected, the gastrostomy tube is placed over the guide wire and is pushed toward the stomach from the patient's mouth until it extends out from the abdominal hole. Again, the gastrostomy tube has a bumper to prevent the tube from passing entirely through the abdominal hole and causing the proximal end to remain in the stomach.

Alternatively, percutaneous gastrostomy placement can be performed using gastropexy methods. Gastropexy wires are inserted into the stomach via the angiocatheter and used to tether the stomach. Standard gastropexy techniques are then used to place the gastrostomy tube over a guide wire inserted only within the stomach.

Even with skilled consultant physicians handling these procedures, complications can occur including tube misplacement, inadvertent injury to surrounding tissues during placement, infections, tube clogging, and tube dislodgement during use. When such complications occur outside of the hospital, patients will often come to a hospital emergency room for help. However, as the gastrostomy procedures require specialized skill in handling, emergency medicine physicians are often unable to perform the necessary procedures, and must instead call upon such specialist consultants, which adds to the overall expense and delay in treating the patient's issue, or risk of further complication or injury if someone lacking sufficient specialized skill attempts to address the issue.

Accordingly, there is a need in the art for a device and method that will allow for placement of a medical device into a patient's body, such as the performance of percutaneous gastrostomies, at the bedside and that will no longer require the expertise and equipment of specialist medical personnel, such as a gastroenterologist or other specialist. It would be advantageous to provide a method and device that would reduce the difficulties associated with installing medical devices inside of a patient's body, including medical instrument carriers, medication carriers, electrodes, probes, catheters and other conduits, and more particularly a gastrostomy tube, and that would thereby reduce the risks of injury associated with previously known methods and devices.

DESCRIPTION OF THE INVENTION

Disclosed herein is a system and method for placement of a catheter, conduit, or other elongate member, and more particularly a gastrostomy tube, within a patient's body. Such system and method are suitable for use in therapeutic interventional and/or diagnostic procedures, and may be useful for placement of medical devices, including catheters or other conduits, in varied tissue planes and cavities in a patient's body, including by way of non-limiting example the thorax, abdomen, blood vessels, and pericardium, for diagnostic, therapeutic, and/or procedural purposes. For example, such system and method may be useful in the placement of a catheter within a patient's stomach during a procedure for placement of a gastrostomy tube. Further, such system and method may be useful in the positioning of a suction tube within a patient's body to remove unwanted fluid. As used herein, all of such carriers, catheters, conduits, delivery devices, internal probes and sensors, electrodes, and the like that are intended for insertion into a patient's body are referred to generally as "elongate medical members."

By allowing visual confirmation through the use of readily-available ultrasound equipment, internal catheter, conduit, or other elongate medical member placement can be achieved without the need for expensive, specialized equipment, such as endoscopes, fluoroscopes, and CT scanners. Thus, the system and method disclosed herein will enable acute care physicians, such as emergency medicine physicians and critical care physicians (i.e., intensivists), or other healthcare providers trained in the art of ultrasound, to place such catheters, conduits, and other elongate medical members safely and reliably.

With regard to certain aspects of an embodiment of the invention, the system and method may be used for inserting gastrostomy tubes in a simple bedside procedure without requiring the use of specialized consultants or specialized equipment including endoscopes, fluoroscopes, and CT scanners. The system and method make use of more widely available medical devices that require less specialized training to use, such as ultrasounds, feeding tubes, guide wires, and dilators. By allowing a wider population of medical operators to perform such procedures, the system and method disclosed herein offer safer, more immediate and more cost-effective care. For example, unlike endoscopes, ultrasound ensures that an adequate window for percutaneous gastrostomy tube insertion is present by providing visual confirmation that no bowel, organs, or blood vessels obstruct the cannulation tract between the skin surface and the stomach wall. Further, with this procedure, emergency medicine physicians may easily re-insert dislodged gastrostomy tubes and immediately discharge patients back to their residence instead of admitting them for traditional gastrostomy placement to be performed by a specialist consultant, thus saving time and decreasing consultation costs, hospital admission costs, patients' stress, and the risk of nosocomial infection. Geriatricians and rehabilitation physicians may likewise use the system and method disclosed herein in nursing home and rehabilitation facilities. This practice could dramatically reduce overall costs by eliminating patient transportation costs and thus avoiding all hospital fees.

In accordance with certain aspects of an embodiment, methods and devices are disclosed herein for inserting a gastrostomy tube into a patient. In one exemplary embodiment, a device is provided comprising a flexible tube having a distal end and proximal end, wherein the distal end comprises an inner balloon and an outer balloon, wherein the inner balloon communicates with a first port at the proximal end of the device via a first lumen, and the outer balloon communicates with a second port at the proximal end of the device via a second lumen, wherein the outer balloon is configured to form around the inner wall of a patient's stomach when inflated, and wherein the space between the outer and inner balloon is configured to create an echogenic window when filled with a fluid. In another example embodiment, the device further comprises a snare head within the inner balloon, wherein the snare head communicates with a snare release at the proximal end of the device via a cord that runs the length of the device. In alternative embodiments, a snare is not provided. Instead, one or more of the balloons are configured to receive and couple with a guidewire. In combination with the balloon functionality, guidewires are employed that have tips that are capable of coupling with the conduit. One example configuration is a deployable anchor. The deployable anchor may take the form of a "T" shape or a bulky knot that forms once inside the coupling balloon. Other deployable anchor types may also be used. In other embodiments, the device further comprises one or more rivets between the inner and outer balloon to prevent the echogenic window from collapsing. In yet other embodiments, the inner balloon of the device has one or more ridges that creates one or more cavities between the outer balloon and the inner balloon.

Single balloon configurations of the device are also provided.

In other embodiments a kit is provided for inserting an elongate medical member, such as a gastrostomy tube, into a patient in need comprising an ultrasound device, a double balloon conduit, a guidewire, an angiocatheter and an elongate medical member, such as a gastrostomy tube.

Methods of ultrasound guided guidewire insertion for, for example, gastrostomy tube placement are also provided comprising: inserting the distal end of a double balloon conduit into a patient's body (e.g., into a patient's stomach through their mouth); attaching the necessary pumps to the device; inflating the outer balloon and inner balloon with one or more gases or liquids to create an echogenic window; using an ultrasound probe in conjunction with the echogenic window to identify an acceptable location on the patient's body to insert the guidewire; inserting an angiocatheter into that location under ultrasound guidance; inserting a guidewire into the incision; capturing the distal end of the guidewire; deflating the balloon assembly; and retracting the device from the patient's body.

BRIEF DESCRIPTION OF THE DRAWINGS

The numerous advantages of the present invention may be better understood by those skilled in the art by reference to the accompanying figures in which.

BEST MODE(S) FOR CARRYING OUT THE INVENTION

The invention summarized above may be better understood by referring to the following description, claims, and accompanying drawings. This description of an embodiment, set out below to enable one to practice an implementation of the invention, is not intended to limit the preferred embodiment, but to serve as a particular example thereof. Those skilled in the art should appreciate that they may readily use the conception and specific embodiments disclosed as a basis for modifying or designing other methods and systems for carrying out the same purposes of the present invention. Those skilled in the art should also realize that such equivalent assemblies do not depart from the spirit and scope of the invention in its broadest form.

Figure 1:
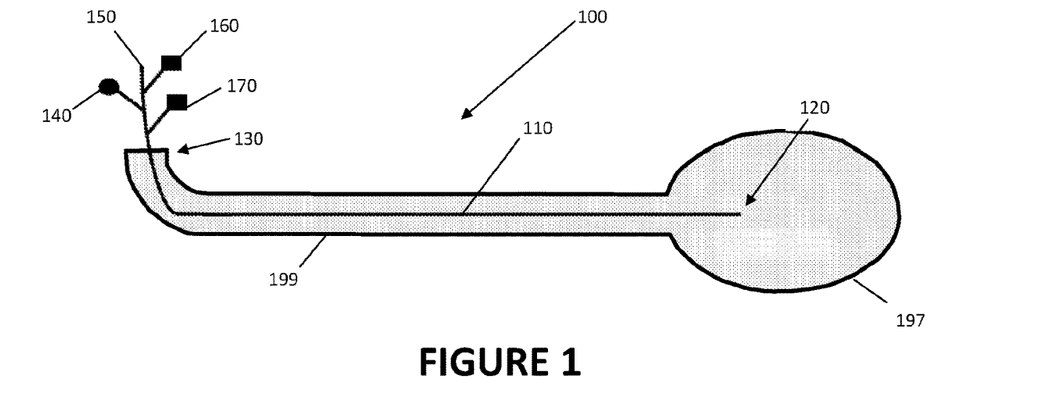
FIG. 1 is a schematic view of an example double balloon conduit device of the present invention.

FIG. 1 is a schematic view of the double balloon conduit 100. Conduit 100 includes a flexible tube 110 having a distal end 120 and a proximal end 130. The flexible tube 110 is preferably sized to extend from the patient's mouth to the distal end of the patient's stomach. In the figure the patient's stomach is marked as 197 and the esophagus is marked as 199. These elements are not part of the invention but rather are included for illustrative purposes.

Proximal end 130 includes a sump port 150, inner balloon port 160, and outer balloon port 170. Sump port 150 communicates with one or more sump fenestrations 355 (FIGS. 3 and 4) located at the distal end 120 of the double balloon conduit 100. One or more central lumens extend the length of the double balloon conduit 100 to allow for passage of fluid, gases, or other material between the distal end 120 and outside of the patient. The sump port 150 may be configured to communicate with a manual or mechanical pumping system to assist with the removal of debris. Inner balloon port 160 communicates with an inner balloon 260 located at the distal end 120 of the double balloon conduit 100. One or more lumens extend the length of the double balloon conduit 100 to allow for the inner balloon 260 to be inflated or deflated. The inner balloon port 160 may be connected to an external fluid handler (e.g., a pump) to inject or remove fluid or gas from the inner balloon 260. Outer balloon port 170 communicates with an outer balloon 270 at the distal end 120 of the double balloon conduit 100 via one or more lumens that run the length of the double balloon conduit 100. Outer balloon port 170 may also be connected to a pump to inject or remove fluids or gasses from the outer balloon 270. In certain embodiments, the inner balloon pump and outer balloon pump are programmed to run in tandem with each other so that the balloons 260 and 270 will expand and contract in tandem with each other. The pumps may also be programed to pump to a predetermined pressure to ensure proper expansion of the balloons 260 and 270.

FIG. 1 also illustrates optional snare release 140. The snare release communicates with a snare head located at the distal end of the double balloon conduit in embodiments that are configured to snare. Such snare configurations and snare releases 140 are of well-known construction to those skilled in the art, and thus are not further detailed here.

Figure 2:
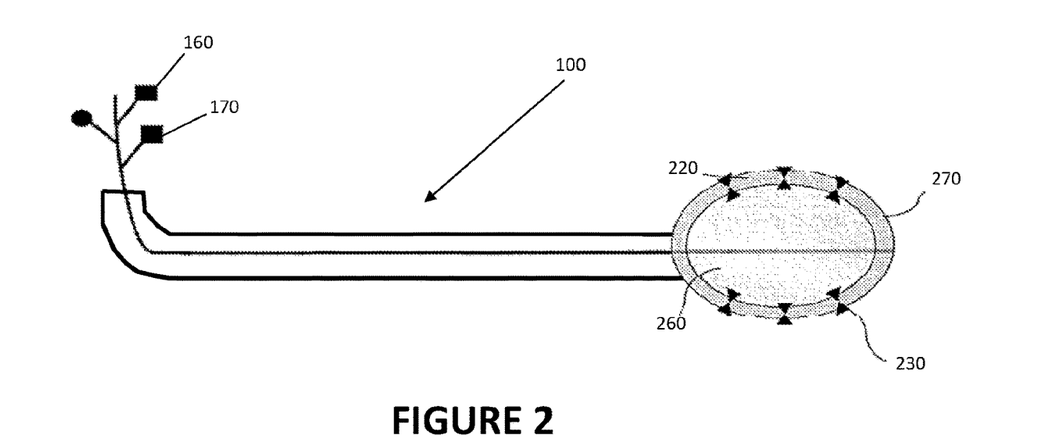
FIG. 2 is a schematic view of the double balloon conduit with a deployed balloon assembly.

FIG. 2 is an expanded schematic view of the double balloon conduit 100 while a balloon assembly is deployed. In the illustrated embodiment, inner balloon 260 is nested within outer balloon 270 and inflated. The outer balloon 270 is configured to expand to the inner surface of the patient's stomach when insufflated via the outer balloon port 170. The shape of the inner balloon 260 and outer balloon 270 may vary provided that the outer balloon 270 is sized to contact the inner surface of a patient's stomach at the location in which the gastrostomy tube is to be placed. The shape of the balloons 260 and 270 also allow for one or more cavities 220 between the inner balloon 260 and outer balloon 270 when inflated.

In preferred embodiments, the outer balloon 270 is filled with a fluid, such as water, saline, or other ultrasound-compatible fluid, and the inner balloon 260 is filled with a fluid that may be the same fluid as in the outer balloon or a different fluid, such as air or other non-toxic gas. When the cavity 220 between inner balloon 260 and outer balloon 270 is filled with ultrasound-compatible fluid, it provides an echogenic window for safely placing the gastrostomy tube. The echogenic window and ultrasound placement improves visualization of subcutaneous tissues and the inner balloon 260 and outer balloon 270 beneath the subcutaneous tissues, and prevents accidental piercing of the bowel, vessels, spleen, liver, or other organs that could jeopardize the health of the patient. By creating one or more echogenic windows 220 between inner balloon 260 and outer balloon 270 and placing the PEG tube by ultrasound, an operator may easily ensure that insertion of an angiocatheter into a patient's stomach is carried out at the intended location and with minimal risk of inadvertently piercing other organs or patient tissues.

Different mechanisms are provided herein to prevent the inner balloon 260 from eliminating the echogenic window by coming into contact with the outer balloon 270. In certain embodiments, one or more spacers, such as rivets 230, are provided between the two balloons 260 and 270. The rivets 230 maintain the preferred distance between the inner and outer balloons 260 and 270. The rivets 230 may be located around the entire surface of the inner balloon 260 or just the area where the echogenic window is desired.

Figure 3:
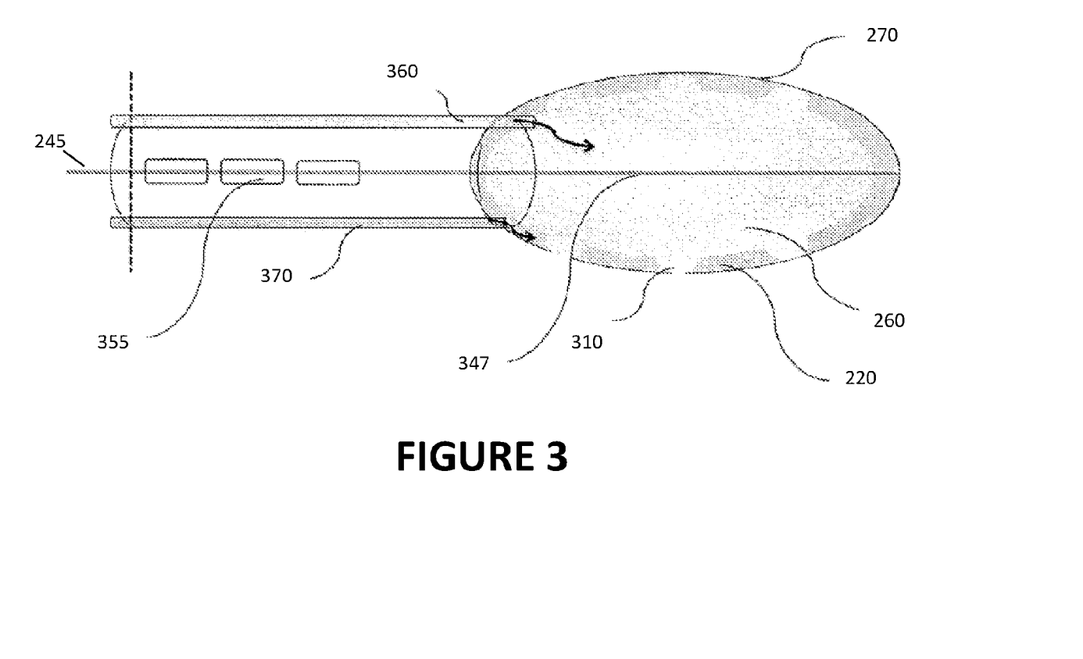
FIG. 3 illustrates an example distal end of the device with a deployed balloon assembly, in which the inner balloon includes ridges to prevent the collapse of the echogenic window.

Alternatively, one or both of balloons 260 and 270 may themselves incorporate spacers that are configured to maintain cavities 220 between the two balloons 260 and 270. FIG. 3 is an exploded view of the distal end of the double balloon conduit 100 having a deployed balloon head. Inner balloon 260 incorporates spacers in the form of one or more ridges 310 that maintain the desired spacing between inner balloon 260 and outer balloon 270. The size, number and location of the ridges 310 may vary depending on the application, such as location within the patient and purpose for placement. In other non-illustrated embodiments, the material properties of the inner and outer balloons 260 and 270 are chosen to maintain the spacing between the two balloons 260 and 270 when deployed. For example, stiffer materials can be employed to prevent the migration of the inner balloon 260 as it is filled with air. Another example configuration includes an expandable frame within the inner balloon 260 that will prevent the inner balloon 260 from contacting the outer balloon 270. Differential pressurization of the balloons 260 and 270 can also be used to obtain the desired configuration and response.

FIG. 3 illustrates other features of the distal end 120 of the double balloon conduit 100. In certain embodiments, snare 245 of traditional configuration extends through the inner balloon 260 and includes a snare head 347 to capture elements passing through the balloons 260 and 270. Sump fenestrations 355 are also illustrated, extending through a sidewall of flexible tube 110. The fenestrations 355 may vary in size, shape and orientation, depending on the patient needs. In certain embodiments, two or more fenestrations 355 are provided to reduce the likelihood of clogging.

Inner balloon tubing 360 and outer balloon tubing 370 allow for balloons to communicate with their respective ports 160 and 170 at the proximal end of the double balloon conduit 100. In the illustrated embodiment, a single tube for each of balloon 260 and 270 is provided. However, in alternative embodiments, two or more tubes may be used to supply each balloon 260 and 270. Multiple tubes may be preferred when there are multiple cavities between the inner balloon 260 and outer balloon 270. Separate tubes may be used to provide different pressures within the cavities 220 or when the cavities 220 are completely independent of the others.

Figure 4:
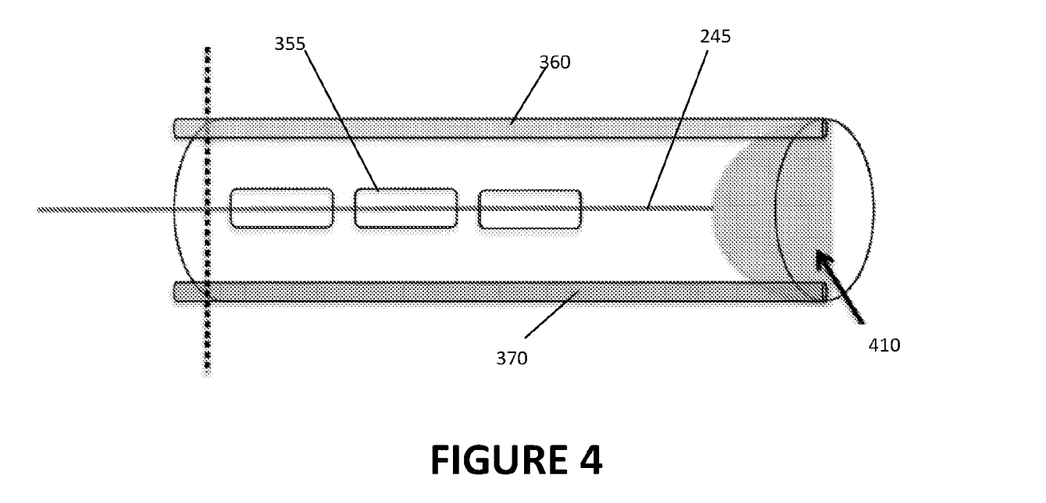
FIG. 4 illustrates an example distal end of the device with a retracted balloon assembly.

FIG. 4 is an exploded view of the distal end 120 of the double balloon conduit 100 with the inner balloon 260 and outer balloon 270 retracted. The balloon assembly 410 (including, in combination, inner balloon 260 and outer balloon 270) is configured to retract within the distal end 120 of the double balloon conduit 100 to make it low profile and help facilitate passage of the double balloon conduit 100 into and out of the stomach. In certain embodiments, the balloon assembly 410 is connected to a cord that runs the length of the double balloon conduit 100 to the proximal end 130. This cord is used to fully retract the balloon assembly 410 after inflation. In other embodiments, the snare release 140 can be configured to perform this task.

Additional features of the double balloon conduit 100 may be used to help secure the guidewire to the distal end 120 of the double balloon conduit 100 and also ensure the guidewire is pulled through the patient as the double balloon conduit 100 is removed. For example, guidewires having anchoring features may be used. In this case, the distal tip of the guidewire can expand or otherwise change shape to help create an anchor inside one or both of the balloons 260 and 270. One example anchor is a "T" shape and another is a bulky knot. In such configuration, the anchor may be inserted into inner balloon 260 before inner balloon 260 is deflated. Thus, as inner balloon 260 is deflated, it surrounds the anchor within inner balloon 260, such that pulling double balloon conduit 100 out of the patient's mouth or nose will likewise cause inner balloon 260 to pull the anchor, along with the attached guidewire.

Other anchoring devices would be recognized in the field and do not deviate from the spirit of the invention. Alternatively, or in conjunction with the anchor, the guidewire may have a magnetic tip that is configured to communicate with, or attract, a magnetic tip that can be added to the distal end 120 of the double balloon conduit 100. This magnetic attraction can also help facilitate passage through the patient.

Single balloon configurations are also provided. In certain single balloon examples, the balloon is configured to expand until at least a portion of the balloon's outer face is resting against at least a portion of the inner wall of the patient's stomach. The balloon is configured to expand when it is filled with fluid or another echogenic material. When the balloon is sufficiently full it creates an echogenic window for ultrasound guided guidewire placement. In other single balloon configurations, the balloon has one or more pouches on its surface that are configured to fill with fluid or another echogenic material. When the balloon is sufficiently inflated with a gas, the one or more pouches are pressed against the wall of the stomach. When filled, the pouches create an echogenic window for ultrasound guided guidewire placement. In another single balloon configuration, the balloon's pouches are made from echogenic materials and do not require infusion with echogenic materials.

Figure 5:
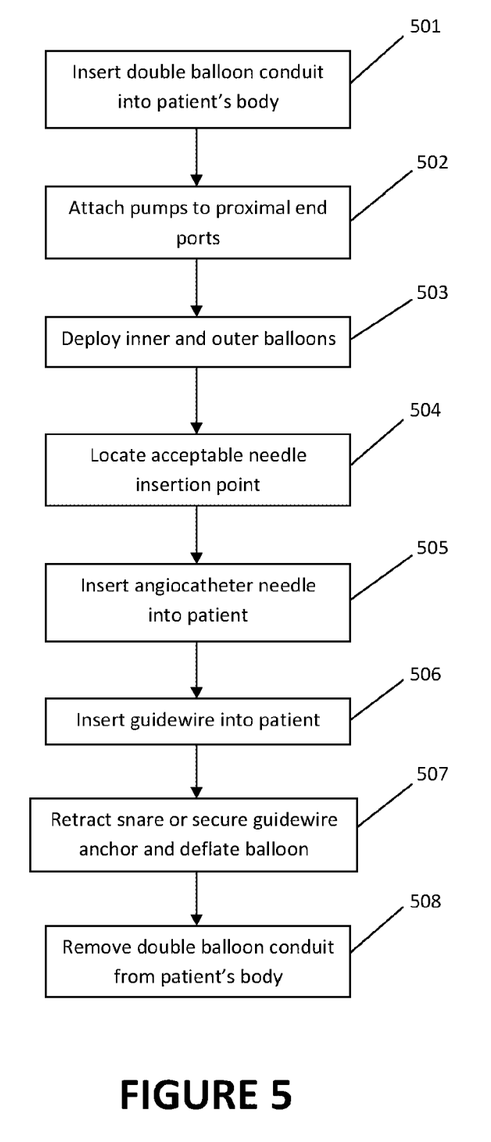
FIG. 5 is a flow chart that demonstrates one method of using the double balloon conduit device.

FIG. 5 is a flow chart that depicts the steps for inserting a guidewire into a patient for placement of an elongate medical member, such as a gastrostomy tube, using a device according to at least certain aspects of and embodiment of the present invention. In step 501, the distal end 120 of the double balloon conduit 100 is passed into the patient's mouth and down into the patient's stomach. Next, in step 502, the pumps are attached to the sump port 150 and inner and outer balloon ports 160 and 170. Outer balloon 270 and inner balloon 260 are deployed in step 503. The order of the balloon deployment will generally depend on the configuration of the double balloon conduit 100. In certain embodiments, the inner and outer balloons 260 and 270 will deploy simultaneously, while in other embodiments, the inner balloon 260 will be filled first with a fluid and then the one or more cavities 220 between the inner and outer balloons 260 and 270 will be filled with a fluid to form an echogenic window.

In step 504, an ultrasound probe will be used to select an appropriate location for inserting the angiocatheter needle. More particularly, an ultrasound probe will be used to detect the location of the echogenic window between inner balloon 260 and outer balloon 270. Step 505 includes inserting the angiocatheter into the stomach once a location is identified that is clear of obstructions. Inserting the needle is monitored by ultrasound.

Step 506 includes inserting the guidewire into the stomach through at least one of the balloons 260 and 270. In embodiments that include a snare, the guidewire passes through the snare head in order to be captured. In embodiments that use a snare, step 507 includes retracting the snare 245 into the distal end 120 of the double balloon conduit 100, thereby securing the guidewire. When using a device that utilizes a guidewire anchor, the guidewire anchor is deployed or secured inside one or more of the balloons 260 and 270. The balloon assembly 410 is then emptied/deflated and retracted into the distal end 120 as well. In step 508 the entire assembly is removed from the patient's mouth. The guidewire can then be used to insert a gastrostomy tube using known techniques.

Figure 6A:
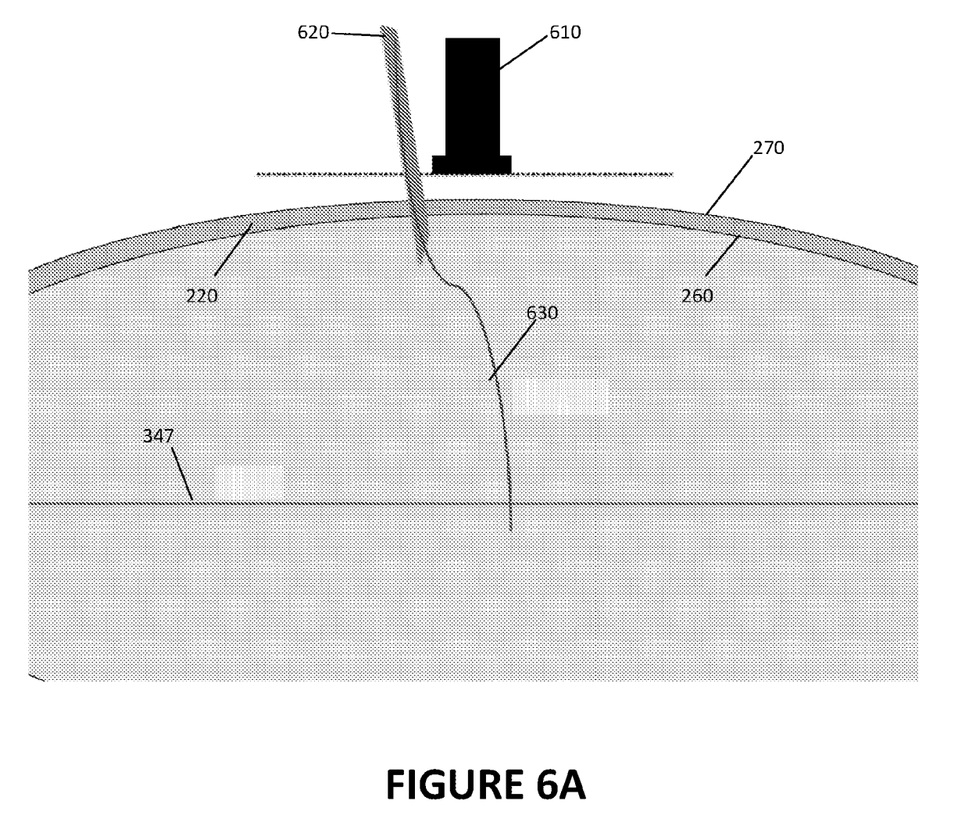
FIG. 6A-C illustrate the method steps described in FIG. 5.
Figure 6B:
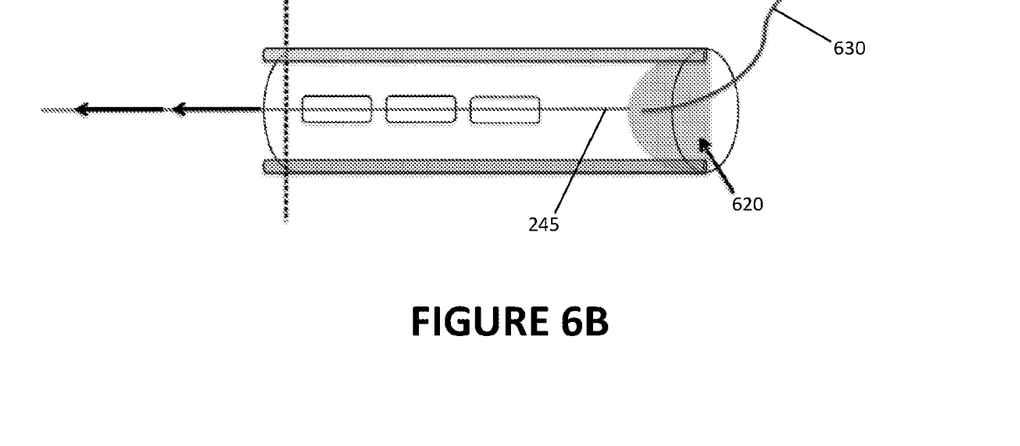
Figure 6C:
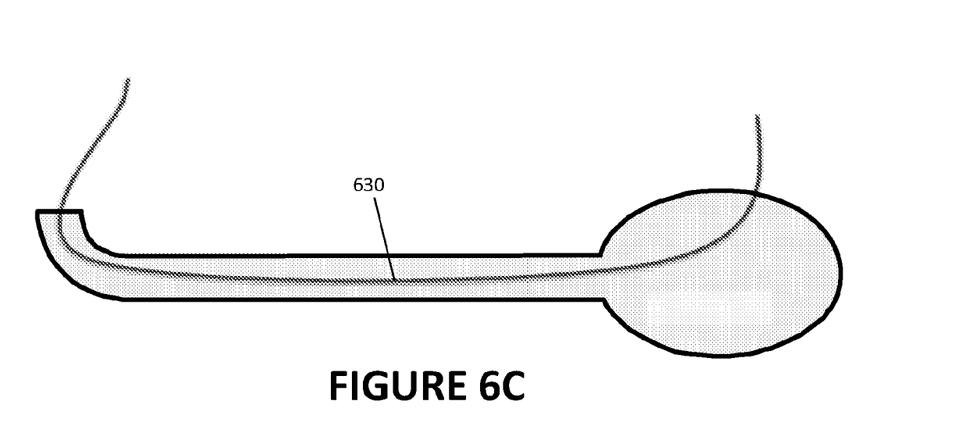

The steps described above and in FIG. 5 are partially illustrated in FIGS. 6a-6c. FIG. 6a shows a deployed outer balloon 270 and inner balloon 260. Cavities 220 are filled with water or saline to create an echogenic window. Ultrasound probe 610 is used to identify an appropriate site of entry for the angiocatheter needle, 620, and guidewire, 630. FIG. 6b shows the distal end 120 of the double balloon conduit 100 after the guidewire 630 has been captured by the snare and the balloon assembly 410 has been retracted. FIG. 6c shows the guidewire 630 remaining after the device has been removed from the patient's mouth.

In the foregoing specification, the invention has been described with reference to specific embodiments thereof. It will, however, be evident that various modifications and changes may be made thereto without departing from the broader spirit and scope of the invention. The specification and drawings are, accordingly, to be regarded in an illustrative rather than a restrictive sense. Throughout this specification and the claims, unless the context requires otherwise, the word "comprise" and its variations, such as "comprises" and "comprising," will be understood to imply the inclusion of a stated item, element or step or group of items, elements or steps but not the exclusion of any other item, element or step or group of items, elements or steps. Furthermore, the indefinite article "a" or "an" is meant to indicate one or more of the item, element or step modified by the article.

Having now fully set forth the preferred embodiments and certain modifications of the concepts underlying the present invention, various other embodiments as well as certain variations and modifications of the embodiments herein shown and described will obviously occur to those skilled in the art upon becoming familiar with said underlying concepts. It should be understood, therefore, that the invention may be practiced otherwise than as specifically set forth herein.

INDUSTRIAL APPLICABILITY

The present invention is applicable to devices and methods for placing medical devices into patients, particularly through ultrasound-guided placement. The devices can be made in industry and practiced in the medical device field.

What is claimed is:

1. A method, comprising:
   translating a distal end of an elongated member into a cavity of a patient to dispose a first inflatable member and a second inflatable member within the cavity, the first inflatable member and the second inflatable member coupled to the elongated member, the second inflatable member disposed within an interior of the first inflatable member;
   delivering echogenic fluid through a first lumen defined within the elongated member to a space between an inner surface of the first inflatable member and an outer surface of the second inflatable member to expand the first inflatable member to define an echogenic interior volume between the inner surface of the first inflatable member and the outer surface of the second inflatable member;
   delivering an inflation fluid to an interior of the second inflatable member through a second lumen defined within the elongated member to expand the second inflatable member, the second lumen being fluidically isolated from the first lumen within the elongated member; and
   visualizing the echogenic interior volume within the cavity using an ultrasound probe disposed on an opposite side of a tissue plane from the cavity.

2. The method of claim 1, further comprising:
   advancing a distal end of a guidewire through the tissue plane and through a sidewall of the first inflatable member.

3. The method of claim 2, further comprising:
   advancing the distal end of the guidewire to pierce and pass through a sidewall of the second inflatable member.

4. The method of claim 2, further comprising:
   contracting the first inflatable member; and
   translating the elongated member to cause the first inflatable member to pull the distal end of the guidewire from the cavity.

5. The method of claim 4, wherein the contracting includes deflating the first inflatable member.

6. The method of claim 2, further comprising:
   contracting the first inflatable member; and
   translating the elongated member to pull the distal end of the guidewire to an exterior of the patient such that the distal end and a proximal end of the guidewire are disposed outside of the patient and a portion of the guidewire is disposed in the cavity.

7. The method of claim 1, wherein a plurality of spacers are disposed between the first inflatable member and the second inflatable member.

8. The method of claim 7, wherein each spacer from the plurality of spacers includes a ridge disposed on the outer surface of the second inflatable member.

9. The method of claim 1, further comprising:
   advancing a needle through the tissue plane and through a sidewall of the first inflatable member; and
   advancing a distal end of a guidewire through the needle and into an interior of the first inflatable member.

10. The method of claim 1, wherein the cavity is a stomach of the patient.

11. The method of claim 1, wherein the echogenic fluid and the inflation fluid are different fluids.

12. The method of claim 1, wherein the echogenic fluid includes at least one of water or saline.

13. The method of claim 1, wherein the space between the inner surface of the first inflatable member and the outer surface of the second inflatable member is fluidically isolated from the interior of the second inflatable member, and a plurality of spacers are disposed between the first inflatable member and the second inflatable member.

14. The method of claim 1, wherein the elongated member includes a first port associated with the first lumen and a second port associated with the second lumen, the first port and the second port configured to be disposed outside of the patient when the distal end of the elongated member is disposed within the cavity.

15. The method of claim 1, wherein the space between the inner surface of the first inflatable member and the outer surface of the second inflatable member includes a plurality of cavities.

16. The method of claim 15, wherein the delivering the echogenic fluid through the first lumen includes delivering a first portion of the echogenic fluid to a first cavity from the plurality of cavities, and further comprising delivering a second portion of the echogenic fluid to a second cavity from the plurality of cavities.

17. A method, comprising:
translating a distal end of an elongated member into a cavity of a patient to dispose a first inflatable member and a second inflatable member within the cavity, the first inflatable member and the second inflatable member coupled to the elongated member, the second inflatable member disposed within an interior of the first inflatable member, a plurality of spacers being disposed between the first inflatable member and the second inflatable member, each spacer from the plurality of spacers including a rivet disposed between an inner surface of the first inflatable member and an outer surface of the second inflatable member;
expanding the first inflatable member and the second inflatable member to define an echogenic interior volume between the inner surface of the first inflatable member and the outer surface of the second inflatable member; and
visualizing the echogenic interior volume within the cavity using an ultrasound probe disposed on an opposite side of a tissue plane from the cavity.

* * * * *